United States Patent [19]

Giobbio

[11] 4,228,283

[45] Oct. 14, 1980

[54] PROCESS FOR PREPARING PURE 2-METHYL-3-(β-HYDROXYETHYLCARBAMOYL)QUINOXALINE 1,4-DI-N-OXIDE, AND OTHER COMPOUNDS SIMILAR THERETO

[75] Inventor: Vincenzo Giobbio, Loranze' di Ivrea, Italy

[73] Assignee: Marxer S.p.A., Loranze', Italy

[21] Appl. No.: 18,516

[22] Filed: Mar. 8, 1979

[30] Foreign Application Priority Data

Nov. 24, 1978 [IT] Italy .............................. 69686 A/78

[51] Int. Cl.² ........................................ C07D 241/44
[52] U.S. Cl. ........................................ 544/355
[58] Field of Search ........................ 544/355, 35

[56] References Cited

U.S. PATENT DOCUMENTS

| | | | |
|---|---|---|---|
| 3,600,388 | 8/1971 | Durkheimer | 544/355 |
| 3,660,391 | 5/1972 | Ley | 260/250 QN |
| 3,682,906 | 8/1972 | Seng | 544/355 |
| 3,948,911 | 4/1976 | McFarland | 260/250 QN |
| 4,039,540 | 8/1977 | Pirlam | 544/355 |
| 4,092,415 | 5/1978 | Schmid et al. | 544/355 |

FOREIGN PATENT DOCUMENTS 1308370  2/1973  United Kingdom .

OTHER PUBLICATIONS

Elina et al., Chem. Abs. 85, 63031m (1976).

*Primary Examiner*—Mark L. Berch
*Attorney, Agent, or Firm*—Fleit & Jacobson

[57] ABSTRACT

The present invention provides a process for preparing high purity 2-methyl-3-(β-hydroxyethylcarbamoyl)-quinoxaline 1,4-di-N-oxide, generally involving the following stages carried out separately and in succession:

(a) reacting benzofuroxane with an acetacetic acid ester of formula $CH_3—CO—CH_2—COOR$, in the presence of a catalyst in the form of ethanolamine, and in a suitable solvent;

(b) separating and isolating the reaction product formed under (a), e.g., 2-methyl-3-(methylcarboxylate)-quinoxaline-1,4-di-N-oxide; and (c) reacting the compound described under (b) with an excess of ethanolamine over the stoichiometric quantity, to give the final carbamoyl derivative.

11 Claims, No Drawings

PROCESS FOR PREPARING PURE 2-METHYL-3-(β-HYDROXYETHYLCAR-BAMOYL)QUINOXALINE 1,4-DI-N-OXIDE, AND OTHER COMPOUNDS SIMILAR THERETO 2-methyl-3-(β-hydroxyethylcarbamoyl)quinoxaline 1,4-di-N-oxide is a substance possessing chemotherapeutic activity, its field of action being directed particularly towards the prevention and cure of special bacterial infections in animals.

Its formula is as follows:

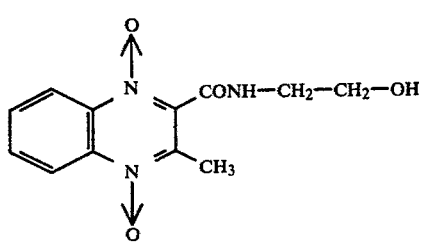

This substance is known, and is described for example in the following patent literature: Ley, Eholzer etc.; U.S. Pat. No. 3,660,391 (1972); Fr. M 8123 (1970); DT 1 670 935 (1967); Cronin, Timoty, Ger. Offen 2,212,932 (1972); Kasubick, Valentine, Robertson, Lee, Ger. Offen 2,215,320 (1972); McFarland, Jannes W. U.S. Pat. No. 3,948,911 (1976); Kasubick, Valentine, Ger. Offen. 2,238,208 (1973); Kasubick, Valentine, Robertson, Lee, Fr. Demande 2,132,378; Austrian 315,188 (1974).

In particular, the following methods are known for synthesising compound (VI) and other compounds similar thereto:

Condensing benzofuroxane (I) with an acetacetic acid amide (VII) in accordance with the following equation:

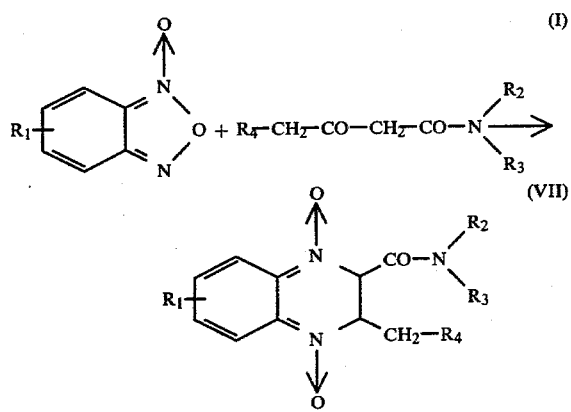

which is described in the following patents: DT 1670935 (1975); Fr. 8123 (1970); Ley, Eholzer, Nast etc. U.S. Pat. No. 3,660,391 (1972).

It is also known to synthesise compound (VI) and the like starting from benzofuroxane (I), the methyl ester of acetacetic acid (II) and ethanolamine (V) in a single stage in accordance with the following equation:

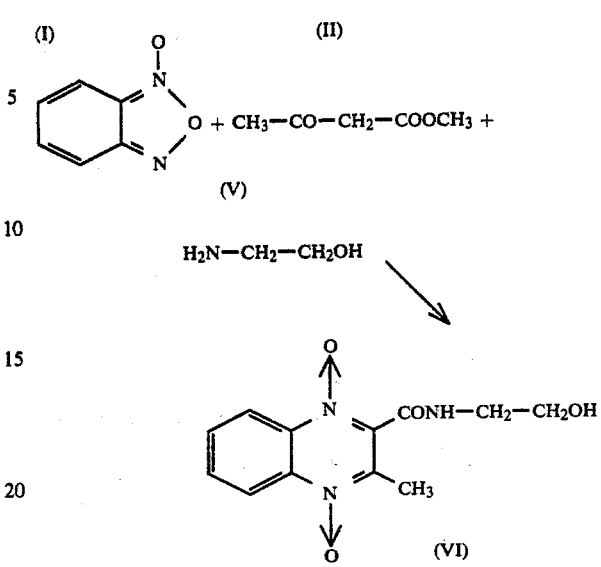

This synthesis is described in the following patents: McFarland, James W. U.S. Pat. No. 3,948,911 (1976); Abuel-Haj, Marwan J., Cronin, Timoty H., Ger. Offen 2,035,480 (1971).

A substantial disadvantage of these known processes, and in particular of this latter process, is that a rather impure final product is obtained, which is difficult to purify. Thus the yield from this process or from the others heretofore described is not satisfactory. The object of the present invention is to overcome such problems, by providing a process for preparing high purity 2-methyl-3 (β-hydroxyethyl-carbamoyl) quinoxaline 1,4-di-N-oxide, comprising the following stages carried out separately and in succession:

(a) reacting benzofuroxane with an acetacetic acid ester of formula $CH_3-CO-CH_2-COOR$, in the presence of a catalyst in the form of ethanolamine, and in a suitable solvent;

(b) separating and isolating the reaction product formed under (a), e.g., 2-methyl-3-(methylcarboxylate)-quinoxaline-1,4-di-N-oxide; and (c) reacting the compound described under (b) with an excess of ethanolamine over the stoichiometric quantity, to give the final carbamoyl derivative.

The scheme of the two reactions given under points (a) and (c) above is as follows:

REACTION stage (a)

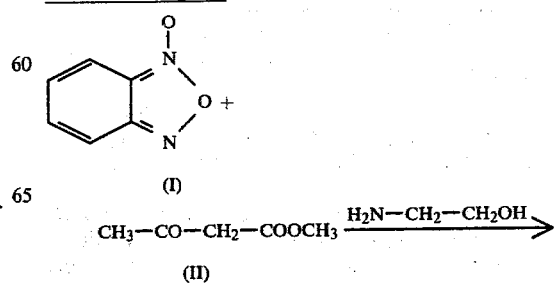

-continued

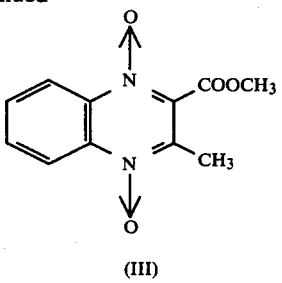

REACTION stage (c)

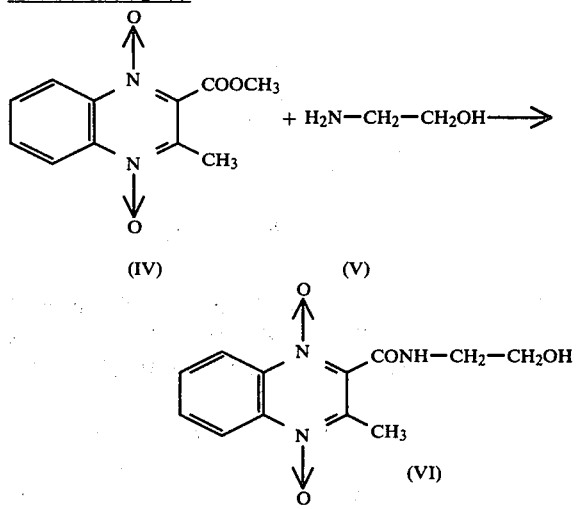

In this scheme, the acetacetic acid ester used is the methyl ester. This ester can however be generally an ester in which R is a $C_1$–$C_6$ alkyl.

The most favourable condition for the proper progress of the reaction described under (a) is to mix the benzofuroxane with the methyl acetoacetate in stoichiometric ratio in the presence of a small quantity of ethanolamine, and a suitable solvent. More particularly, the ratios of the benzofuroxane to the acetacetic acid ester and the solvent, referred to 1 mole of benzofuroxane, lie within the following ranges, respectively:

| Benzofuroxane | ester | ethanolamine | solvent |
|---|---|---|---|
| 1 | 0.5–2 | 0.1–0.8 | 0.5–4 |

The reaction temperature can vary from 10° to 60° C., and the time lies between 24 and 50 hours.

The solvent used can be methanol, ethanol or other higher alcohols; or toluol, xylol or other aromatic hydrocarbons; or alternatively ethers, chlorinated hydrocarbons, dimethylformamide, dimethylsulphoxide or dioxane. However, the alcohols are the most suitable solvents to avoid secondary reactions.

The progress of the reaction under (a) can easily be checked by TLC, using as eluent a mixture of the following composition: chloroform 85, acetonitrile 5, formic acid 7.

On termination of the reaction, the product III is completely precipitated, and can be collected by a pump filter and be used as such for the next reaction, without being dried.

With regard to the reaction described under (c), the most favourable condition is to work in the presence of an excess of ethanolamine, so that the environment is always definitely basic, and the reaction equilibrium is displaced towards the right.

The most suitable solvent has been found to be dimethylformamide, and the reaction temperature must not exceed 55°, and normally lies between 20° and 50° C., however there are considerable variations in the reaction time.

A larger quantity of ethanolamine can be used instead of dimethylformamide, or alternatively the following can be used: dimethylacetamide, dimethylsulphoxide, tetrahydrofurane, dioxane, or other solvents such as methanol, ethanol, propanol, isobutanol or other higher alcohols, ethyl ether, propyl ether, hydrocarbons such as benzene, toluene, xylene, chlorinated solvents such as dichloroethane, chloroform, trichloroethylene, etc.

As already stated, instead of using the compound IV, i.e. 2-methyl-3-(methyl-carboxylate) quinoxaline-1,4-di-N-oxide, the corresponding ethyl or propyl ester or esters of other long chain primary alcohols up to 6 carbon atoms can be used.

On termination of the reaction, the 2-methyl-3-($\beta$-hydroxyethylcarbamoyl) quinoxaline 1,4-di-N-oxide can easily be isolated from the reaction mixture, as it can be collected by filtration because of its poor solubility in nearly all solvents.

The reaction described under stage (c) is carried out by mixing the 2-methyl-3-(methyl-carboxylate) quinoxaline 1,4-di-N-oxide (esterified as described previously) with a large excess of ethanolamine over the stoichiometric quantity and in the presence of a solvent chosen from those stated heretofore.

The reaction mixture is kept at 20° to 25° C. for 50–100 hours, after which the precipitate, which forms as fine crystals, is collected by a pump filter.

The product is normally very pure. It can be determined by u.v., and is visible under TLC using an eluent having the following composition: chloroform 85, acetonitrile 5, formic acid 7.

The use of a catalytic quantity of ethanolamine in the reaction under stage (a) therefore enables the alkylcarboxylate intermediate of formula (III) to be obtained with a high purity and a high purity and a high yield.

The only impurity substantially present is a small quantity of ethanolamine. However, as an excess of ethanolamine is used under stage (c) of the process, the problem of purifying the intermediate (III) at the end of said stage (b) does not arise.

If more ethanolamine is used in said stage (a) than the quantity stipulated according to the present invention, the final compound of formula (VI) would inevitably be formed during the initial stage, thus creating the problem of purifying the intermediate (III) before the reaction under (c). In addition to negatively influencing the process yield, this would be absolutely undesirable because of the great difficulty in purifying the derivative (III) from the final product (VI).

The described process can also be applied to other amines to obtain various amides, in accordance with the following scheme:

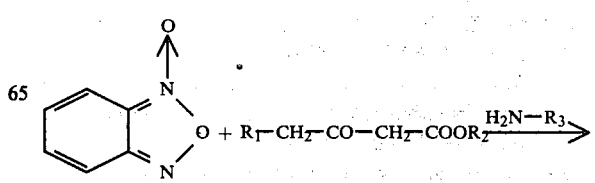

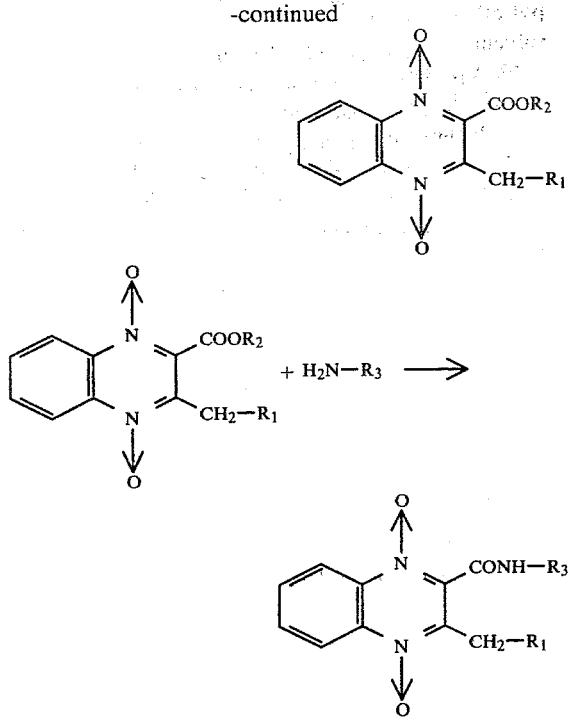

in which $R_1$, $R_2$, $R_3$ can be alkyl radicals of various chain lengths, or aryl radicals.

The methods according to the invention will be more apparent from some examples of application given below, but which must not be considered as limiting.

EXAMPLE 1

PREPARATION OF 2-METHYL-3 (ALKYL-CARBOXYLATE)-QUINOXALINE-1,4-DI-N-OXIDE 13.6 g (0.1 moles) of benzofuroxane and 11.6 g (0.1 moles) of methyl acetoacetate are placed in a flask fitted with a stirrer and heater.

13 ml of methanol and 3 g of ethanolamine are then added.

The mixture is heated to 40°–45° for approximately 24 hours.

The progress of the reaction is checked by TLC (eluent: chloroform 85, acetonitrile 5, formic acid 7).

The quantity of benzofuroxane present in the mother liquor is checked by a gas chromatograph on termination of the reaction, and must be less than 1%.

At this point, pump filtration is applied. The precipitate is subsequently used as such.

The product contains 8% of moisture, and when dried has an M.P. of 133°.

The yield obtained is 20.6 g (88% of the theoretical).

EXAMPLE 2

PREPARATION OF 2-METHYL-3 (β-HYDROXYETHYLCARBAMOYL) QUINOXALINE 1,4-DI-N-OXIDE 23.4 g (0.1 moles) of 2-methyl-3-(methyl-carboxylate) quinoxaline-1,4-di-N-oxide, 36.6 g (0.6 moles) of ethanolamine and 37 ml of dimethylformamide are placed in a flask fitted with a stirrer and heater.

The mixture is heated to 45° and kept at this temperature for 48 hours.

The progress of the reaction is checked by TLC (eluent: chloroform 85, acetonitrile 5, formic acid 7).

After this time, a sample is taken and a TLC check is made to see whether the starting substance is still present.

When this latter has almost disappeared, pump filtration is applied, and the product dried under vacuum to give 24 g of the required product, with a yield of 91.2%.

The product thus obtained has an M.P. of 217° C., and a purity of 99%.

EXAMPLE 3

23.4 g (0.1 moles) of 2-methyl-3-(methyl-carboxylate) quinoxaline-1,4-di-N-oxide, 36.6 g (0.6 moles) of ethanolamine and 24 ml of methanol are placed in a flask fitted with a stirrer and heater.

The mixture is heated to 45° and kept at this temperature until termination of the reaction, which is followed by TLC (eluent: chloroform 85, acetonitrile 5, formic acid 7).

72 hours are normally required for termination of the reaction.

At this point, the product is collected by a pump filter and dried under vacuum. 18 g of the product are obtained, with a yield of 69% of the theoretical.

What we claim is:

1. A process for preparing high purity 2-methyl-3-(β-hydroxyethyl-carbamoyl) quinoxaline 1,4-di-N-oxide, comprising the following stages carried out separately and in succession:
   (a) reacting benzofuroxane with an acetacetic acid ester of formula $CH_3-CO-CH_2-COOR$ in which R is a $C_1-C_6$ alkyl radical, in the presence of a catalyst in the form of ethanolamine, and in a suitable solvent;
   (b) separating and isolating the 2-methyl-3-(alkylcarboxylate)quinoxaline-1,4-di-N-oxide reaction product formed in stage (a); and
   (c) reacting the reaction product isolated in stage (b) with an excess of ethanolamine over the stoichiometric quantity to give the carbamoyl derivative.

2. A process as claimed in claim 1, wherein in said stage (a) the stoichiometric ratio of the benzofuroxane to ethanolamine is 1:0.1–0.5.

3. A process as claimed in claim 1, wherein said stage (a) is carried out at a temperature of 10° to 60° C.

4. A process as claimed in claim 3, wherein in said stage (a) the stoichiometric ratios of the benzofuroxane to the acetacetic acid ester and the solvent, referred to 1 mole of benzofuroxane, are within the following ranges:

| Benzofuroxane | ester | ethanolamine | solvent |
|---|---|---|---|
| 1 | 0.5–2 | 0.1–0.8 | 0.5–4 |

5. A process as claimed in claim 4, wherein said solvent is methanol, ethanol, aliphatic alcohols higher than 6 carbon atoms, toluol, xylol, esters, chlorinated hydrocarbons, dimethylformamide, dimethylsulphoxide or dioxane.

6. A process as claimed in claim 5, wherein said solvent is methanol, and the stoichiometric ratios of the benzofuroxane to the ester, the ethanolamine and the methanol are 1:1:0.50:1, respectively.

7. A process as claimed in claim 1, wherein said stage (c) is carried out at a temperature of 10° to 60° C.

8. A process as claimed in claim 7, wherein in said stage (c), the stoichiometric ratio of the carboxylate intermediate separated during stage (b) to the ethanolamine is such that, for each mole of carboxylate intermediate, the number of moles of ethanolamine is in the range of 2 to 20.

9. A process as claimed in claim 8, wherein said stage (c) is carried out in the presence of a solvent selected from the group consisting of ethanolamine, dimethylformamide, dimethylacetamide, dimethylsulphoxide, tetrahydrofurane, dioxane, an alcohol, ethyl ether, propyl ether, benzene, toluene, xylene and a chlorinated solvent.

10. A process as claimed in claim 9, wherein the quantity of solvent used in said stage (c) is 1 to 20 moles per mole of said carboxylate intermediate.

11. A process as claimed in claim 9, wherein said alcohol is methanol, ethanol, propanol or isobutanol and said chlorinated solvent is dichloroethane, chloroform or trichloroethylene.

* * * * *